US008060232B2

(12) United States Patent
Kuntz et al.

(10) Patent No.: US 8,060,232 B2
(45) Date of Patent: Nov. 15, 2011

(54) POTTED INSERT INSTALLATION AND VALIDATION

(75) Inventors: Michael P. Kuntz, Snohomish, WA (US); Mark L. Younie, Snohomish, WA (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 684 days.

(21) Appl. No.: 12/138,971

(22) Filed: Jun. 13, 2008

(65) Prior Publication Data

US 2009/0326702 A1    Dec. 31, 2009

(51) Int. Cl.
 *G06F 19/00* (2006.01)
 *G01B 3/00* (2006.01)
 *G01F 1/00* (2006.01)
 *G01F 7/00* (2006.01)
(52) U.S. Cl. .......... 700/110; 700/95; 700/108; 700/109; 702/33; 702/45; 702/46
(58) Field of Classification Search .................... 700/110
 See application file for complete search history.

(56) References Cited

U.S. PATENT DOCUMENTS

| | | | |
|---|---|---|---|
| 3,510,916 A * | 5/1970 | Phelan | 425/110 |
| 5,796,619 A * | 8/1998 | Wampler | 700/195 |
| 5,876,024 A * | 3/1999 | Hain | 267/141.4 |
| 5,898,590 A * | 4/1999 | Wampler et al. | 700/174 |
| 6,153,035 A * | 11/2000 | Van Laeken | 156/73.5 |
| 2004/0055248 A1* | 3/2004 | Grillos | 52/783.1 |
| 2004/0102709 A1* | 5/2004 | Tanaka | 600/459 |
| 2006/0162456 A1* | 7/2006 | Kennedy et al. | 73/620 |

OTHER PUBLICATIONS

Olympus, BondMaster, Probes and Accessories Catalog, Innovation in NDT Apr. 23, 2008, 24 pages.*

* cited by examiner

*Primary Examiner* — Albert DeCady
*Assistant Examiner* — Sunray Chang
(74) *Attorney, Agent, or Firm* — Hope Baldauff Hartman, LLC

(57) ABSTRACT

Methods and computer storage media provide for the installation of potted inserts and installation validation. According to embodiments described herein, an insert is placed within an insert aperture of a panel or other structure. Potting compound is injected into a potting cavity surrounding the insert through a fill hole in the insert until potting compound overflows from another fill hole. The installation is validated by applying a force to the installed insert at a determined frequency using a mechanical impedance instrument and measuring a response frequency. The response frequency is compared to an acceptable frequency range to determine whether the insert is properly installed.

13 Claims, 7 Drawing Sheets

POTTED INSERT INSTALLATION AND VALIDATION

BACKGROUND

Commercial aircraft interior assembly often involves utilizing attachment inserts (hereinafter "inserts") installed within aircraft panels using a potting compound. The installed inserts are then utilized to attach adjacent panels or other structures to the panel in which the insert is installed. However, due to the laminate sandwich structure of typical panels, insert apertures drilled into the panel for the inserts are not uniform in volume. In other words, the honeycomb-like structure of the panel core creates cells, voids, and inconsistencies from one insert aperture to the next, preventing installation of the inserts using a pre-measured quantity of potting compound.

As a result, a typical insert installation involves placing a quantity of potting compound in an insert aperture prior to installing an insert. The insert is then placed into the partially filled insert aperture. Additional compound is then injected into the insert aperture containing the insert through a fill hole in the top of the insert until excess potting compound overflows from a second fill hole in the top of the insert. Finally, to ensure potting compound fully fills the insert aperture, additional potting compound is then injected into the second fill hole until excess potting compound overflows from the first fill hole. This process, while often effective, is tedious in that it requires a technician to fill a single insert aperture three times to ensure that the insert is properly installed.

It is with respect to these considerations and others that the disclosure made herein is presented.

SUMMARY

It should be appreciated that this Summary is provided to introduce a selection of concepts in a simplified form that are further described below in the Detailed Description. This Summary is not intended to be used to limit the scope of the claimed subject matter.

Methods and computer storage media described herein provide for the installation of potted inserts into a panel or other structure and for the validation of proper insert installation. Utilizing the concepts provided herein, a technician or automated machinery can rely on a single injection of potting compound into an insert aperture containing an insert and receive an immediate indication as to whether or not the insert has been properly installed. The single injection and instant validation decreases the number of steps required for insert installation while maintaining a high degree of confidence of proper installation.

According to one aspect of the disclosure provided herein, an insert is positioned within an insert aperture of a structure and potting compound is injected into the insert aperture through a fill hole of the insert until the potting compound exits another fill hole of the insert. A mechanical impedance instrument is then used to determine whether the insert is properly installed. The instrument applies a low frequency vibration to the insert and measures a response frequency to validate the installation.

According to another aspect of the disclosure provided herein, insert installation validation is performed by inserting a tip of an impedance probe into the insert. The tip is specifically sized to engage the insert so that the probe is properly centered over the insert and in contact with the insert. A low frequency vibration is then applied to the insert via the probe and the response frequency is measured. If the response frequency is within a pre-determined acceptable frequency range determined from measuring the response frequencies of a number of properly installed and improperly installed test insert installations, then the installation is validated as being correct. If not, then the insert was improperly installed. According to various implementations, the installation and validation processes described herein may be implemented utilizing computer-controlled apparatus or systems and as a computer process.

The features, functions, and advantages that have been discussed can be achieved independently in various embodiments of the present invention or may be combined in yet other embodiments, further details of which can be seen with reference to the following description and drawings.

DETAILED DESCRIPTION

The following detailed description is directed to methods and computer storage media for installing and verifying proper installation of potted inserts within a panel or other structure. As discussed briefly above, a typical installation of an insert into panel involves adding potting compound into the insert aperture of the panel multiple times to ensure that the insert is properly installed. Even doing so, there are currently no procedures for verifying that the insert was properly installed other than a visual indication of potting compound overflow from the insert.

Utilizing the concepts and technologies described herein, a technician or computer-controlled machinery can apply potting compound to the insert within the panel a single time and then quickly and easily verify that the proper amount of potting compound has been applied using a mechanical impedance instrument. Throughout this disclosure, embodiments are described with respect to installation of an insert within an aircraft panel constructed as a laminate sandwich structure having a honeycomb-like core. It should be understood that the concepts presented herein are equally applicable to any type of insert installed within any type of structure. After calibrating the mechanical impedance instrument in the manner described below, a vibration may be applied to the installed insert at a selected frequency or frequency range in order to measure a response frequency. Whether or not the response is within an acceptable frequency range determines whether or not the insert is properly installed. This procedure is applicable regardless of the characteristics of the structure, the insert, or the potting compound.

Figure 1A:
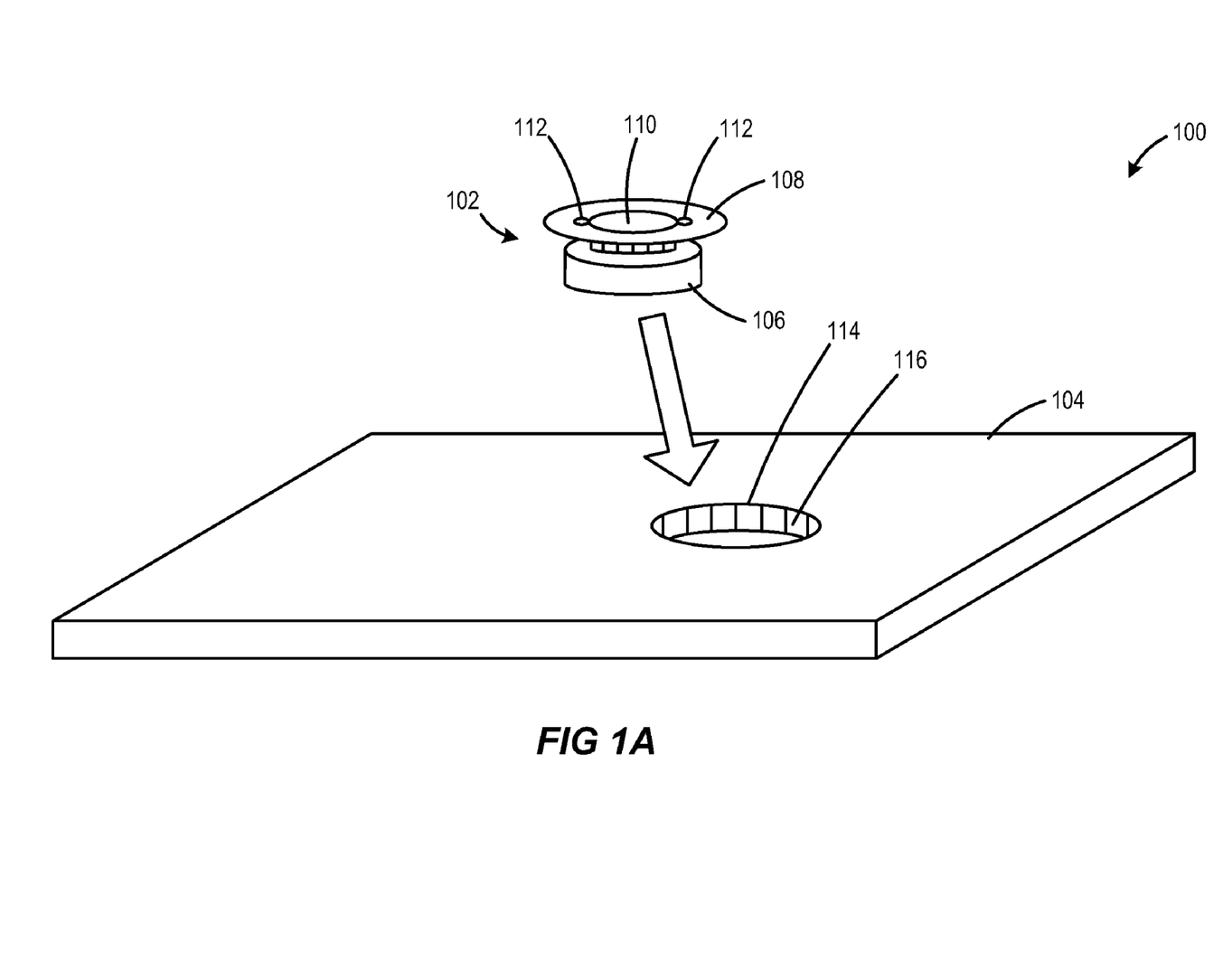
FIG. 1A is a perspective view of an insert and a panel with an insert aperture according to various embodiments presented herein.

In the following detailed description, references are made to the accompanying drawings that form a part hereof, and which are shown by way of illustration, specific embodiments, or examples. Referring now to the drawings, in which like numerals represent like elements through the several figures, potted insert installation and validation will be described. FIG. 1 shows an insert and panel assembly 100 prior to the installation of the insert 102. The insert 102 may be any type of metal or polymer composition insert or insert constructed from any suitable material and of any configuration, including but not limited to a threaded blind insert, a threaded through insert, or a through hole clearance insert.

The insert 102 is to be installed into an insert aperture 114 of a panel 104. The insert aperture 114 is drilled or otherwise formed into the panel 104. It should be appreciated that the insert aperture 114 may traverse the panel 104 from a front side to a rear side of the panel 104, or may be located only on a single side of the panel 104 such that the insert aperture 114 has a depth that is less than the total depth of the panel 104. As discussed above, the panel 104 may have a honeycomb core or a core that is composed of various voids 116 that result in different insert apertures 114 being able to accommodate varying amounts of potting compound.

According to the embodiment shown in FIG. 1, the insert 102 includes an insert body 106, a flange 108, a fastener aperture 110, and fill holes 112. The insert 102 is configured such that when placed within the insert aperture 114, a fill cavity is defined by the space between the insert body 106, an underside of the flange 108, and the walls of the insert aperture 114. The fill cavity may then be filled with potting compound, which when cured, will secure the insert 102 within the panel 104. An adjacent panel or other structure may then be connected to the panel 104 using the fastener aperture 110 of the installed insert 102.

Figure 1B:
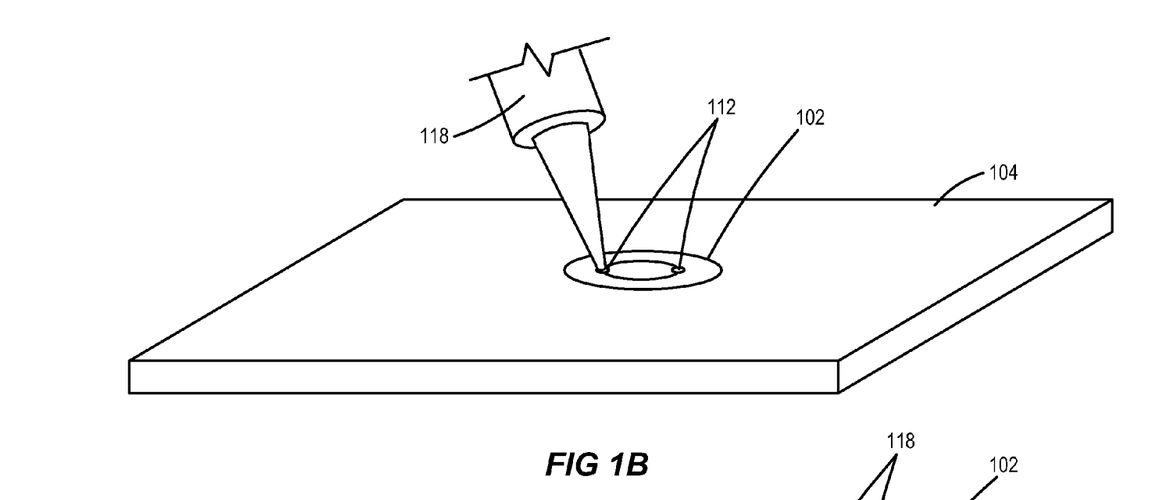
FIG. 1B is a perspective view of a partially installed insert having potting compound injected into the insert aperture according to various embodiments presented herein.
Figure 1C:
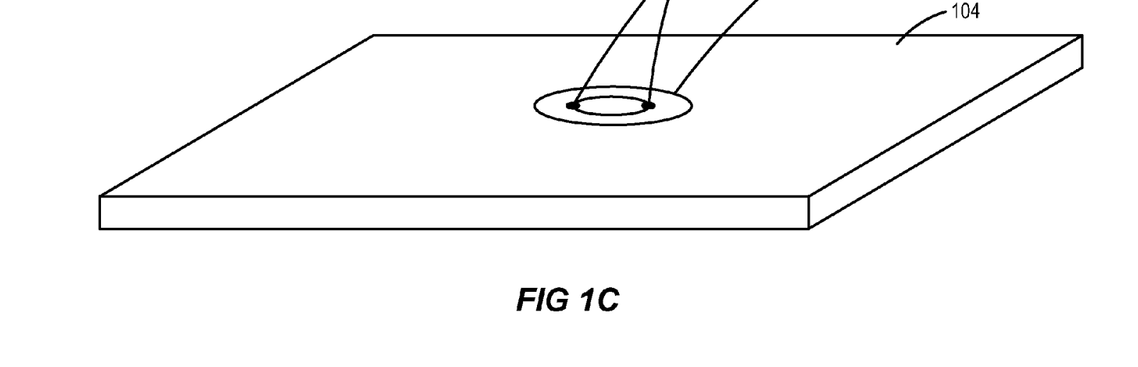
FIG. 1C is a perspective view of a fully installed insert according to various embodiments presented herein.

Looking at FIGS. 1A and 1B, a typical insert 102 installation process, as well as an installation process utilizing the concepts provided herein, will be described. FIG. 1B shows the panel 104 after the insert 102 has been placed within the insert aperture 114. In a typical installation process, potting compound 118 is first placed within the insert aperture 114 before the insert 102. The insert 102 is then positioned within the insert aperture 114 and additional potting compound 118 is injected into the insert aperture 114 through one of two fill holes 112. The potting compound 118 is injected until it exits the insert aperture 114 through the other fill hole 112. The excess potting compound 118 is then wiped away and potting compound is injected into the fill hole 112 through which the excess potting compound exited from the first fill. When overfill exits the insert aperture 114 through the first fill hole 112, the installation process is complete. FIG. 1C shows potting compound 118 occupying the entire fill cavity of the insert aperture 114 up to the fill holes 112.

Due to the rapid installation validation mechanism and process described herein, the installation process is simplified. According to various embodiments, the insert 102 may be positioned within the insert aperture 114 without first adding potting compound 118. The fill process shown in FIG. 1B is simplified to a single step of injecting potting compound 118 into the fill cavity of the insert aperture 114 through a single fill hole 112 until excess potting compound 118 overflows from the other fill hole 112. It should be appreciated that potting compound 118 may be placed within the insert aperture 114 at any time and in any manner without departing from the scope of this disclosure. The efficient manner of validating the installation of the inserts 102 described below allows for potting compound 118 to be injected once since improper installations due to an inadequate amount of potting compound 118 may be quickly and easily discovered and corrected. However, for additional assurance of proper installation, potting compound 118 may be injected multiple times in multiple ways prior to validating the installation.

Figure 2:
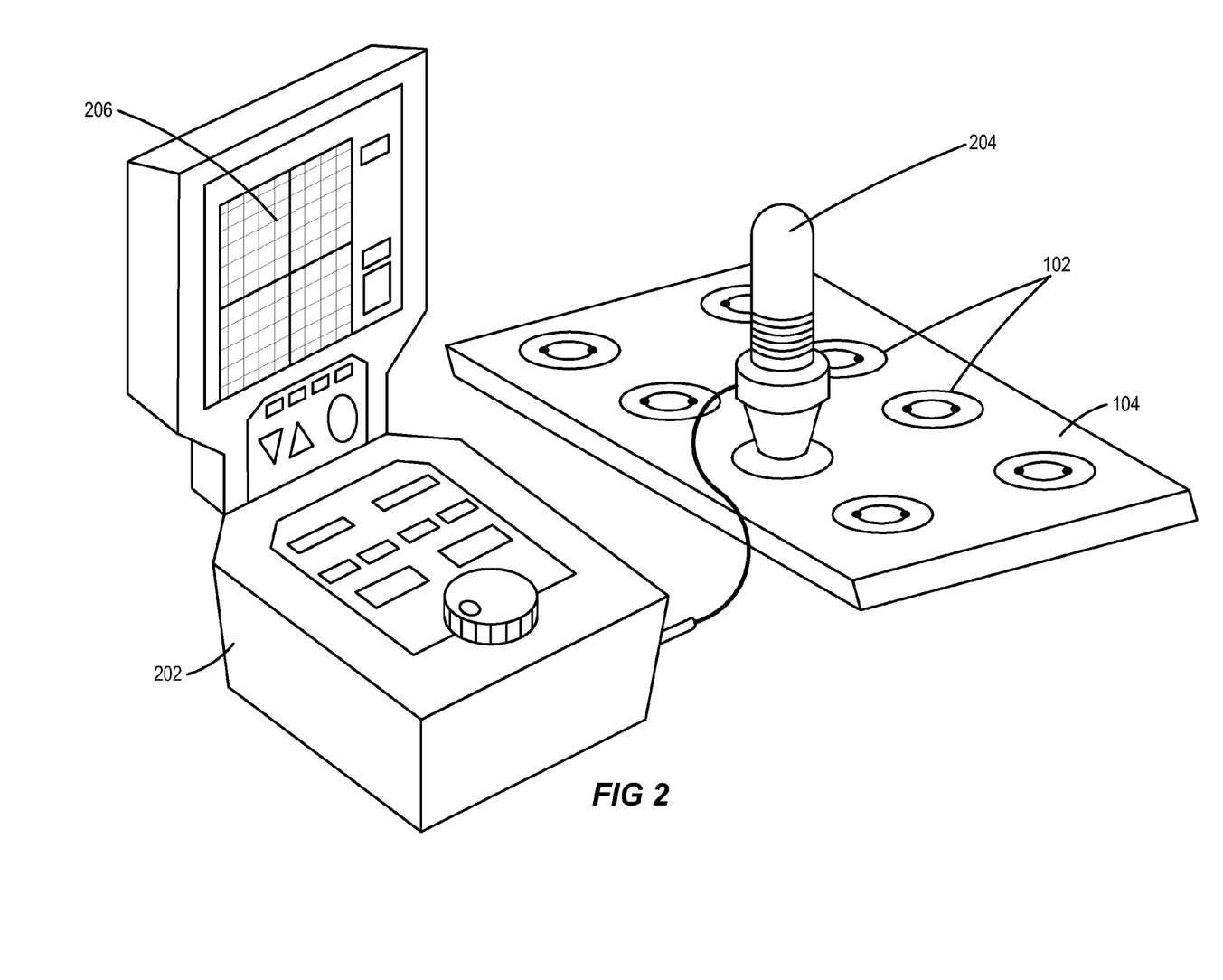
FIG. 2 is an perspective view of a mechanical impedance instrument with a corresponding impedance probe positioned over an installed insert for installation validation according to various embodiments presented herein.

FIG. 2 shows an example of a mechanical impedance instrument 202 with a corresponding impedance probe 204 positioned over an installed insert 102 for installation validation according to various embodiments presented herein. After installing one or more insert 102 in a panel 104, the validity of the installation may be checked using the mechanical impedance instrument 202. To test whether or not an insert 102 is correctly installed, the impedance probe 204 is placed over the installed insert 102. The mechanical impedance instrument 202 applies a low frequency vibration to the surface of the insert 102 via the impedance probe 204. The frequency of the response by the installed insert 102 is then measured by the mechanical impedance instrument 202 via the impedance probe 204. The frequency of the response is used to determine whether the insert 102 is properly installed using an adequate amount of potting compound 118 and the results are presented to the user on a display 206 of the mechanical impedance instrument 202.

It should be understood that any type of mechanical impedance instrument 202 may be used. The mechanical impedance instrument should be able to apply a force or vibration at a known frequency and/or frequency range to the insert 102 and measure the mechanical impedance or frequencies of the resulting response from the insert 102. According to one implementation, the mechanical impedance instrument 202 and corresponding impedance probe 204 include a STAVELY BONDMASTER 1000 and SONIC S-MP-5 probe. Additionally, according to one implementation, the frequency of the applied force is 9 kilohertz, although it should be understood that any suitable frequency may be used depending on the characteristics of the insert 102, panel 104, and/or the potting compound 118.

Figure 3A:
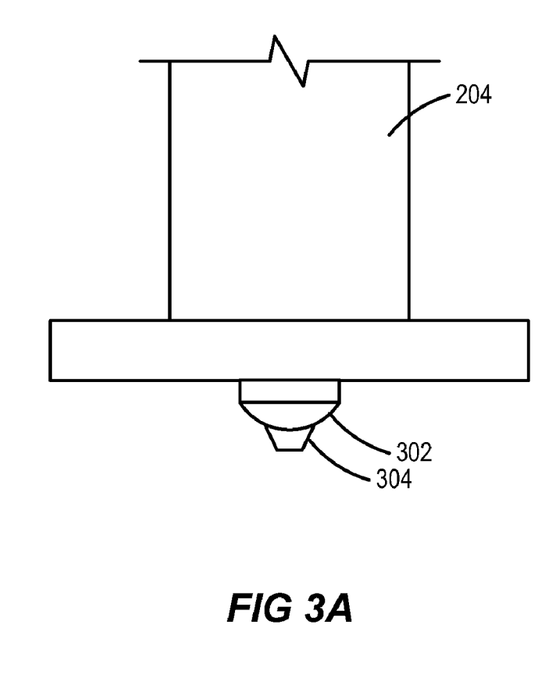
FIG. 3A is a front view of an impedance probe showing the impedance probe tip configured for engagement with an insert according to various embodiments presented herein.
Figure 3B:
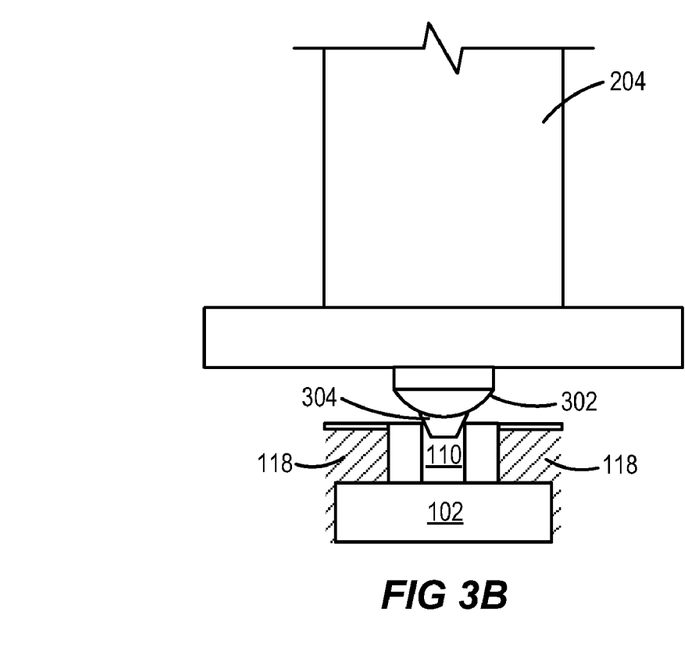
FIG. 3B is a front view of an impedance probe showing the impedance probe tip engaged with an insert according to various embodiments presented herein.

FIGS. 3A and 3B show an illustrative embodiment of an impedance probe 204. The impedance probe 204 includes a force applicator 302 and a conical tip 304. The conical tip 304 is fixedly or removably attached to the force applicator 302, which vibrates at a selected frequency. The conical tip 304 is specifically shaped to engage an insert 102 in a manner that holds the impedance probe 204 in position for testing, preventing the impedance probe 204 from moving along the surface of the panel 104. As seen in FIG. 3B, the conical tip 304 is configured for insertion into the fastener aperture 110 so that the circumference of the conical tip 304 contacts the walls of the fastener aperture 110. It should be understood that the conical tip 304 and the force applicator 302 may be a single component or the impedance probe 204 may be utilized without the use of the conical tip 304 so that the force applicator 302 directly contacts the insert 102. Moreover, the conical tip 304 may be configured in any shape and size corresponding to the fastener aperture 110 of the corresponding insert 102 to be tested.

Figure 4A:
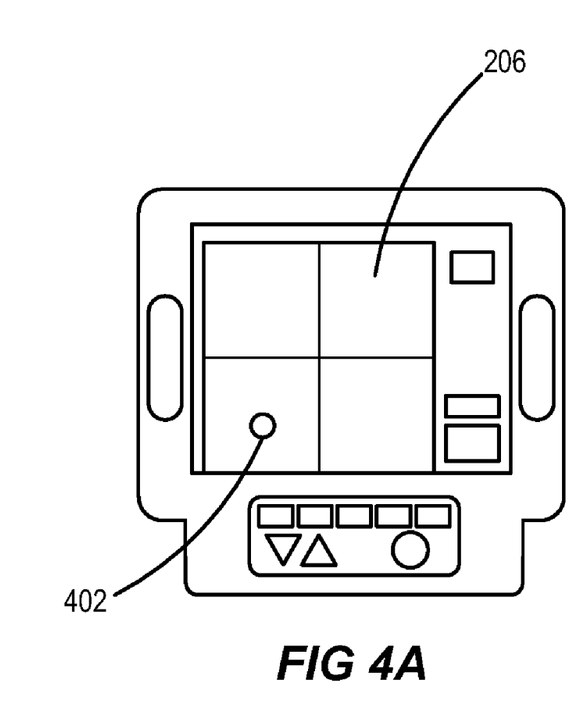
FIGS. 4A and 4B are front views of a mechanical impedance instrument display showing improperly installed and properly installed insert installation validation results, respectively, according to various embodiments presented herein.
Figure 4B:
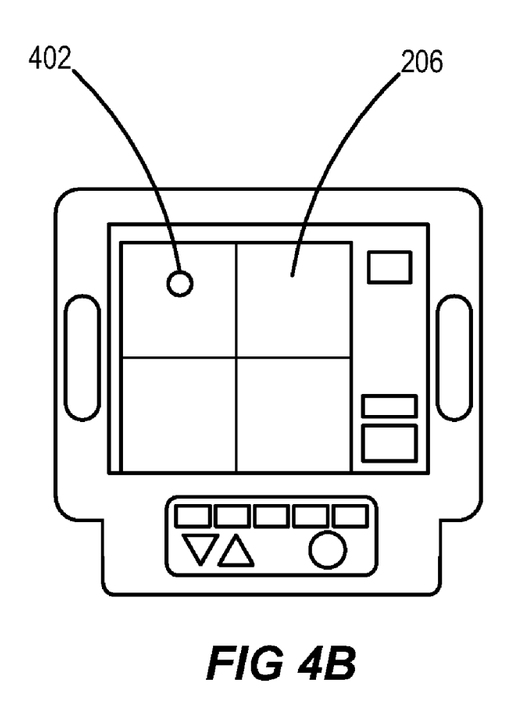

FIGS. 4A and 4B show example notifications of the results of a validation check of an insert 102 installation using the mechanical impedance instrument 202. It should be appreciated that the examples show one of many ways to quickly notify the user whether or not the insert 102 is properly installed. Any number of visual and/or audible notification methods may be utilized. For example, the mechanical impedance instrument 202 may be configured to light up one or more lights, sound an audible alarm, play any type of audio, vibrate, display text, and/or display symbols or other visual representations of proper installations versus improper installations.

According to the embodiment shown in FIGS. 4A and 4B, the vertical position of an indicator 402 within a grid on the display 206 is representative of the installation quality. In this example, the display has been divided in half vertically and horizontally. If the indicator 402 is displayed below the horizontal line, as shown in FIG. 4A, then the insert 102 is improperly installed and correction is required. In this situation, an inadequate amount of potting compound 118 may have been used and additional potting compound 118 may be added to resolve the issue.

In contrast, FIG. 4B shows an example of a proper installation of the insert 102 since the indicator 402 falls above the horizontal reference line. To establish the reference line or other representations of a range of response frequencies that correspond to acceptable response frequencies that, if received from the insert 102 after applying the low frequency vibration to the insert 102, would indicate that the insert 102 is installed correctly, the mechanical impedance instrument 202 is calibrated using known standards. For example, at the beginning of a day or period of use, or when switching between types of inserts 102, panels 104, and/or potting compound 118, a set of reference installations are created. A technician may properly install a number of inserts 102, install a number of inserts 102 without any potting compound 118, and install a number of inserts 102 with an inadequate amount of potting compound 118. Any number and type of known techniques may be used to prepare and validate the reference installations, including but not limited to visual inspections of the installations, x-ray validations, validations using the techniques described herein with a calibrated mechanical impedance instrument 202, and any other known non-destructive inspection and validation techniques.

Using the mechanical impedance instrument 202 and impedance probe 204 being calibrated, a range of vibration frequencies are applied to the inserts 102 that are known to be properly installed to determine a frequency in which the corresponding mechanical impedance of the insert 102 indicates a resonant frequency. The frequency that results in the resonant response frequency is then to be applied to the remaining improperly installed reference inserts 102 to determine and plot a range of response frequencies corresponding to each known "level" of improperly installed insert 102. These response frequencies are used to determine an acceptable range of response frequencies.

When a subsequent insert 102 installation is being tested at the applied frequency that was determined to create a resonant response frequency in a correctly installed insert 102, then the response frequency is compared to the determined acceptable range of response frequencies. If the response frequency falls outside of the acceptable range of response frequencies, then the installation is determined to be faulty and a corrective action is subsequently taken. If the response frequency falls within the acceptable range of response frequencies, then the installation is determined to be correct and the technician or automated machinery may progress to the next insert 102 installation.

Figure 5:
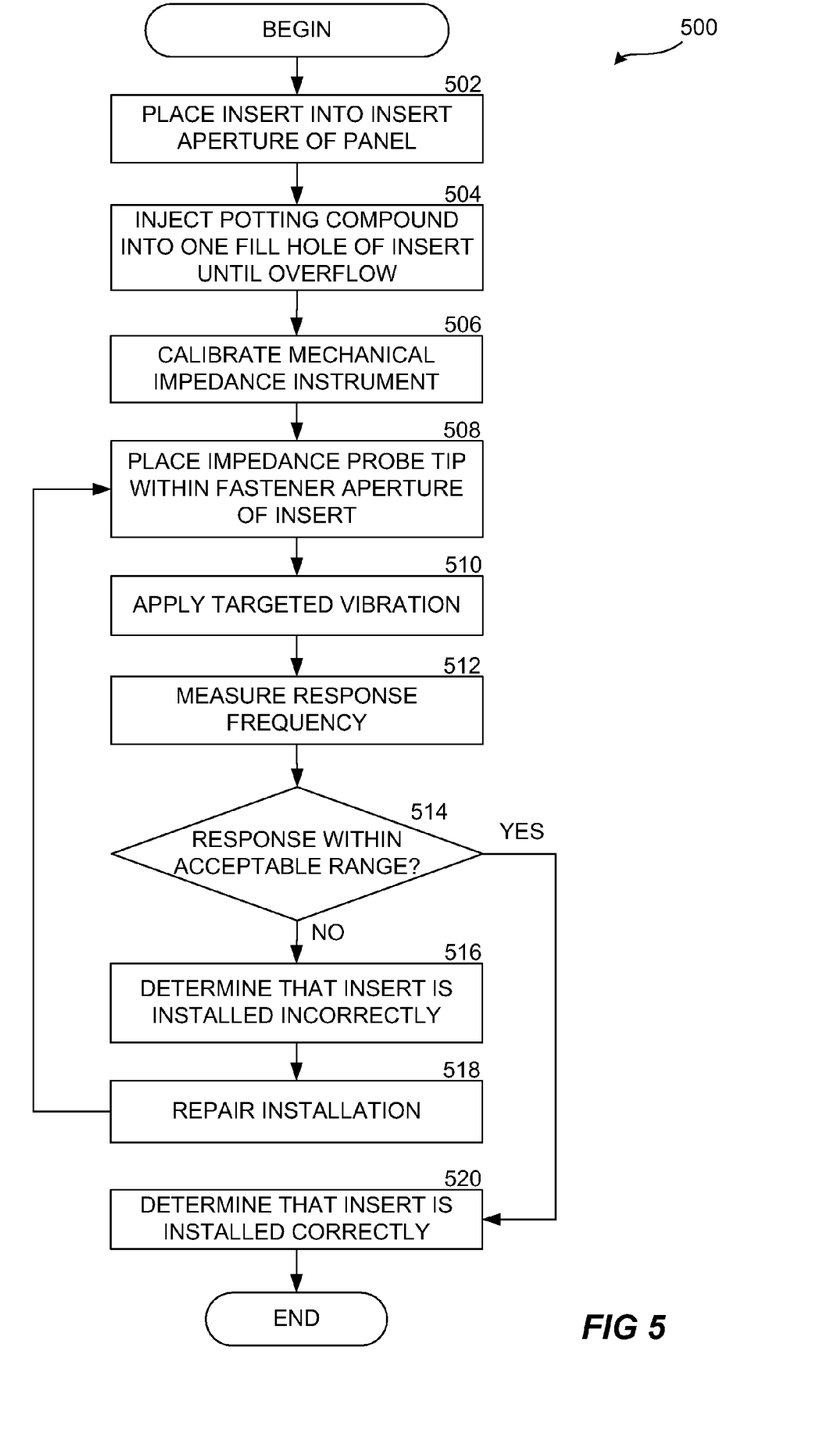
FIG. 5 is a flow diagram illustrating a method for installing and validating the installation of a potted insert according to various embodiments presented herein.

Turning now to FIG. 5, an illustrative routine 500 for installing and validating the installation of a potted insert will now be described in detail. It should be appreciated that the logical operations described herein may be implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states operations, structural devices, acts, or modules. These operations, structural devices, acts and modules may be implemented in software, in firmware, in special purpose digital logic, and any combination thereof. It should also be appreciated that more or fewer operations may be performed than shown in the FIG. 5 and described herein. Moreover, these operations may also be performed in a different order than those described herein.

The routine 500 begins at operation 502, where an insert 102 is placed into an insert aperture 114 of a panel 104. As discussed above, this operation and others may be performed by a technician or more efficiently by computer-controlled machinery. Potting compound 118 is injected into a fill hole 112 of the insert 102 at operation 504 until overflow exits another fill hole 112. From operation 504, the routine 500 continues to operation 506, where the mechanical impedance instrument 202 is calibrated. As described above, the calibration process includes utilizing known standard installations to determine an optimum frequency for application of the force to the insert 102 by the impedance probe 204 and to determine an acceptable range of response frequencies.

The routine 500 continues from operation 506 to operation 508, where the conical tip 304 of the impedance probe 204 is placed within the fastener aperture 110 of the insert 102. A force or vibration is applied to the insert 102 at operation 510 at the frequency determined from the calibration process. From operation 510, the routine 500 continues to operation 512, where the response frequency is measured by the mechanical impedance instrument 202. A determination is made at operation 514 as to whether or not the response frequency is within the acceptable range of response frequencies. If the response frequency is within the acceptable range, then the routine 500 proceeds from operation 514 to operation 520, where it is determined that the insert 102 is installed correctly and the routine 500 ends.

However, if it is determined at operation 514 that the response frequency is not within the acceptable range of response frequencies, then the routine 500 proceeds from operation 514 to operation 516, where it is determined that the insert 102 is not installed correctly. Continuing from operation 516, the installation is repaired at operation 518. According to one embodiment, if it is the first time that the response frequency of the insert 102 being tested is outside of the acceptable range of response frequencies, repairing the installation includes re-injecting potting compound 118 within a fill hole 112 of the insert 102. If the insert 102 installation has been repaired previously, then repairing the installation includes removing the insert 102 and potting compound 118 and re-installing the insert 102 or a new insert 102. After repairing the installation, the routine returns to operation 508 and re-validated with a calibrated mechanical impedance instrument 202 as described above.

Figure 6:
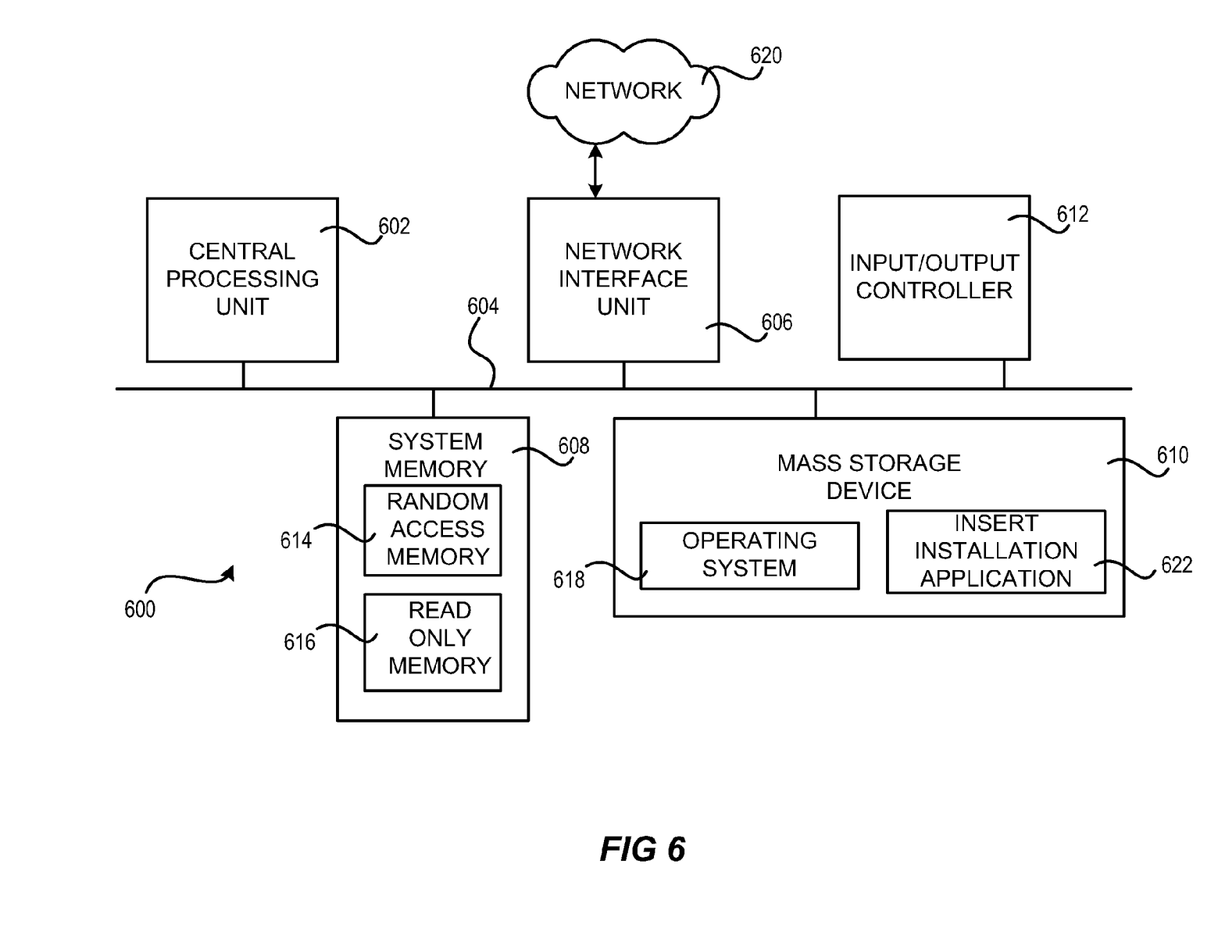
FIG. 6 is a computer architecture diagram showing an illustrative computer hardware and software architecture for a computing system capable of implementing aspects of the embodiments presented herein.

FIG. 6 shows an illustrative computer architecture for a computer 600 capable of executing the software components described herein for providing for insert installation and installation validation according to embodiments described herein. The computer architecture shown in FIG. 6 illustrates a conventional desktop, laptop, or server computer and may be utilized to control apparatus and systems for installing inserts 102 and validating the installations.

The computer architecture shown in FIG. 6 includes a central processing unit 602 (CPU), a system memory 608, including a random access memory 614 (RAM) and a read-only memory (ROM) 616, and a system bus 604 that couples the memory to the CPU 602. A basic input/output system containing the basic routines that help to transfer information between elements within the computer 600, such as during startup, is stored in the ROM 616. The computer 600 further includes a mass storage device 610 for storing an operating system 618, application programs, and other program modules, which are described in greater detail herein.

The mass storage device 610 is connected to the CPU 602 through a mass storage controller (not shown) connected to the bus 604. The mass storage device 610 and its associated computer storage media provide non-volatile storage for the computer 600. Although the description of computer storage media contained herein refers to a mass storage device, such as a hard disk or CD-ROM drive, it should be appreciated by those skilled in the art that computer storage media can be any available computer storage media that can be accessed by the computer 600.

By way of example, and not limitation, computer storage media may include volatile and non-volatile, removable and non-removable media implemented in any method or technology for storage of information such as computer-readable instructions, data structures, program modules or other data. For example, computer storage media includes, but is not limited to, RAM, ROM, EPROM, EEPROM, flash memory or other solid state memory technology, CD-ROM, digital versatile disks (DVD), HD-DVD, BLU-RAY, or other optical storage, magnetic cassettes, magnetic tape, magnetic disk storage or other magnetic storage devices, or any other medium which can be used to store the desired information and which can be accessed by the computer 600.

According to various embodiments, the computer 600 may operate in a networked environment using logical connections to remote computers through a network such as the network 620. The computer 600 may connect to the network 620 through a network interface unit 606 connected to the bus 604. It should be appreciated that the network interface unit 606 may also be utilized to connect to other types of networks and remote computer systems. The computer 600 may also include an input/output controller 612 for receiving and processing input from a number of other devices, including a keyboard, mouse, or electronic stylus (not shown in FIG. 6). Similarly, an input/output controller may provide output to a display screen, a printer, or other type of output device (also not shown in FIG. 6).

As mentioned briefly above, a number of program modules and data files may be stored in the mass storage device 610 and RAM 614 of the computer 600, including an operating system 618 suitable for controlling the operation of a networked desktop, laptop, or server computer. The mass storage device 610 and RAM 614 may also store one or more program modules. In particular, the mass storage device 610 and the RAM 614 may store an insert installation application 622 operative to execute logic for controlling machinery for performing the insert installation and installation validation process described in detail above with respect to FIG. 5. The mass storage device 610 and the RAM 614 may also store other types of program modules.

Based on the foregoing, it should be appreciated that technologies for installing inserts 102 within aircraft panels 104 or other structures and validating the installations are provided herein. The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

What is claimed is:

1. A method for installing an insert in a structure, comprising:
    positioning the insert within an insert aperture of the structure;
    injecting a potting compound into the insert aperture through a first fill hole of a plurality of fill holes externally accessible on an exterior surface of the insert until the potting compound exits the insert aperture via a second fill hole of the plurality of fill holes; and
    determining whether the insert is properly installed utilizing a mechanical impedance instrument that applies a vibration to the insert at a pre-determined frequency and measures a response frequency by
        inserting an impedance probe tip within a fastener aperture of the insert, the impedance probe tip sized to project within the fastener aperture and to engage the insert around a circumference of the impedance probe tip such that the impedance probe tip is prevented from moving along a top surface of the structure when inserted within the fastener aperture,
        applying a low frequency vibration to the insert via the impedance probe tip,
        measuring the response frequency to the low frequency vibration at the impedance probe tip,
        determining whether the response frequency is within a pre-determined acceptable frequency range, and
        if the resonant response frequency is within the pre-determined acceptable frequency range, determining that the insert is properly installed within the insert aperture.

2. The method of claim 1, further comprising:
    if the response frequency is not within the pre-determined acceptable frequency range,
        determining that the insert is not properly installed within the insert aperture,
        injecting additional potting compound into the insert aperture through the first fill hole or second fill hole, and
        re-evaluating whether the insert is properly installed utilizing the mechanical impedance instrument.

3. The method of claim 1, wherein the structure comprises an aircraft panel.

4. The method of claim 1, wherein the insert comprises a blind threaded floating insert, a blind solid threaded insert, or a through threaded insert.

5. The method of claim 1, wherein each of the plurality of fill holes is positioned within a flange of the insert and configured to open to an exterior surface of the insert at a first end and to open at an opposing end to a potting cavity defined by the flange, a body of the insert, and walls of the insert aperture.

6. The method of claim 1, wherein the structure comprises a core structure such that a plurality of insert apertures drilled to equivalent depths accommodates varying quantities of potting compound.

7. The method of claim 1, wherein positioning the insert within the insert aperture of the structure and injecting the potting compound into the insert aperture is performed utilizing automated machinery.

8. The method of claim 7, wherein determining whether the insert is properly installed is performed utilizing automated machinery.

9. A computer storage medium having computer executable instructions stored thereon which, when executed by a computer, cause the computer to:
position an insert within an insert aperture of a structure;
inject a potting compound into the insert aperture through a first fill hole of a plurality of fill holes externally accessible on an exterior surface of the insert until the potting compound exits the insert aperture via a second fill hole of the plurality of fill holes;
insert an impedance probe tip of a mechanical impedance instrument within a fastener aperture of the insert, the impedance probe tip sized to project within the fastener aperture and to engage the insert around a circumference of the impedance probe tip such that the impedance probe tip is prevented from moving along a top surface of the structure when inserted within the fastener aperture;
apply a pre-determined low frequency vibration to the insert via the impedance probe tip;
measure the response frequency to the low frequency vibration at the impedance probe tip;
determine whether the response frequency is within a pre-determined acceptable frequency range; and
if the response frequency is within the pre-determined acceptable frequency range, determine that the insert is properly installed within the insert aperture.

10. The computer storage medium of claim 9, further comprising computer executable instructions stored thereon which, when executed by a computer, cause the computer to:
if the response frequency is not within the pre-determined acceptable frequency range,
determine that the insert is not properly installed within the insert aperture,
inject additional potting compound into the insert aperture through the first fill hole or second fill hole, and re-evaluate whether the insert is properly installed utilizing the mechanical impedance instrument.

11. The computer storage medium of claim 9, wherein the structure comprises an aircraft panel and wherein the insert comprises a blind threaded floating insert, a blind solid threaded insert, or a through threaded insert.

12. A method of validating an installation of an insert within a structure, comprising:
inserting an impedance probe tip of a mechanical impedance instrument within a fastener aperture of the insert, the impedance probe tip sized to project within the fastener aperture and to engage the insert around a circumference of the impedance probe tip such that the impedance probe tip is prevented from moving along a top surface of the structure when inserted within the fastener aperture;
applying a low frequency vibration to the insert with the mechanical impedance instrument via the impedance probe tip;
measuring a response frequency to the low frequency vibration at the impedance probe tip;
determining whether the response frequency is within an acceptable frequency range determined from measuring a plurality of test response frequencies of a plurality of test insert installations of a plurality of properly installed and improperly installed test inserts;
if the response frequency is within the acceptable frequency range, determining that the insert is properly installed within an insert aperture of the structure; and
if the response frequency is not within the acceptable frequency range, determining that the insert is improperly installed within the insert aperture.

13. The method of claim 12, further comprising:
if the response frequency is not within the acceptable frequency range,
injecting potting compound into the insert aperture through a fill hole, and re-evaluating whether the insert is properly installed utilizing the mechanical impedance instrument.

* * * * *